United States Patent
Wallentin

(10) Patent No.: US 6,258,798 B1
(45) Date of Patent: Jul. 10, 2001

(54) METHOD FOR TREATMENT OF UNSTABLE CORONARY ARTERY DISEASE BY AN EARLY REVASCULARISATION TOGETHER WITH ADMINISTRATION OF A LOW MOLECULAR WEIGHT HEPARIN

(75) Inventor: Lars Wallentin, Uppsala (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/391,248

(22) Filed: Sep. 7, 1999

(51) Int. Cl.[7] ................................................. A61K 31/727
(52) U.S. Cl. ................................................................ 514/56
(58) Field of Search .................................................. 514/56

(56) References Cited

PUBLICATIONS

*The Lancet,* vol. 354, pp. 694–695, Aug. 28, 1999.
*The Lancet,* vol. 354, pp. 701–707, Aug. 28, 1999.
*The Lancet,* vol. 354, pp. 708–715, Aug. 28, 1999.
Theroux et al, *N. Engl. J. Med.,* 319–1105–1111 (Oct. 1988).
Theroux et al, *Circulation,* 88:2045–2048 (Nov. 1993).
The RISC Group, *The Lancet,* vol.336, pp. 827–830 (Oct. 1990).
Cohen et al, *Circulation,* 89:81–88 (Jan. 1994).
FRISC Study Group, *The Lancet,* vol. 347, pp. 561–568 (Mar. 1996).
Feldman, *Am. J. Cardiol.,* 59:1187–1190 (1987).
Ambrose et al, *Am. J. Cardiol.,* 51:244–247 (1988).
Williams et al, *Am. J. Cardiol.,* 62:1024–1027 (Nov. 1988).
Gottlieb et al, *N. Engl. J. Med.,* 314:1214–1219 (May 1986).
Larsson et al, *Eur. Heart J.,* 13:207–212 (1992).
Gibson et al, *Circulation,* 73:1186–1198 (Jun. 1986).
Butman et al, *J. Am. Coll. Cardiol.,* 4:667–673 (Oct. 1984).
Sia et al, *Am. J. Cardiol.,* 57:738–744 (Apr. 1986).
Nyman et al, *Am. Heart J.,* 123:324–331 (Feb. 1992).

*Primary Examiner*—Kathleen K. Fonda
(74) *Attorney, Agent, or Firm*—Dinsmore & Shohl LLP

(57) ABSTRACT

The invention relates to a method for treatment of unstable coronary artery disease, which is characterised by an early revascularisation together with administration of a low molecular weight heparin. Preferably the low molecular weight heparin is administered up to revascularisation. The methods are also useful for treatment of unstable angina and not worsening chest pain and for treatment of non-Q-wave myocardial infarction (mild heart attack).

15 Claims, 3 Drawing Sheets

Figure 1:
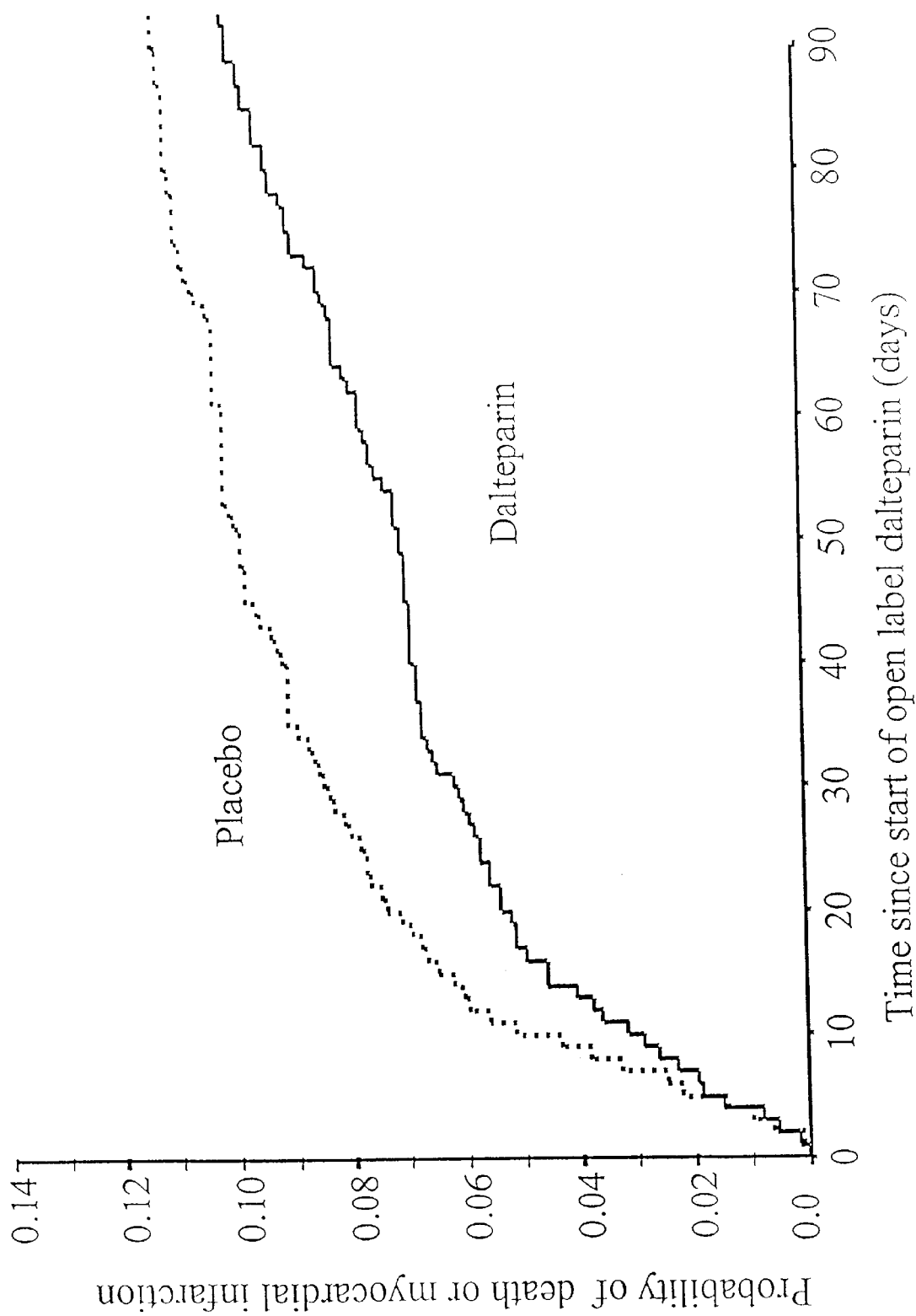

METHOD FOR TREATMENT OF UNSTABLE CORONARY ARTERY DISEASE BY AN EARLY REVASCULARISATION TOGETHER WITH ADMINISTRATION OF A LOW MOLECULAR WEIGHT HEPARIN

INTRODUCTION

The invention relates to a method for treatment of unstable coronary artery disease, which is characterised by an early revascularisation together with administration of a low molecular weight heparin. Preferably the low molecular weight heparin is administered up to revaseularisation.

The methods are also useful for treatment of unstable angina and not worsening chest pain and for treatment of non-Q-wave myocardial infarction (mild heart attack).

BACKGROUND

Heparin is a sulphate-containing polysaccharide, which on a large scale is isolated from intestinal mucus from swine or lung from cattle. It is used as an anti-coagulant medicament. Low molecular weight heparin is obtained by depolymerisation of heparin, normally with a molecular weight of 2000 to 9000 Da. Low molecular weight heparins are clinically used as anti-thrombotic agents.

Fragmin® is a low molecular weight heparin, which has been on the market since 1985 and is manufactured by Pharmacia & Upjohn. It is an antithrombotic agent useful in the treatment and prophylaxis of thrombosis, containing dalteparin sodium with an average molecular weight of 5000 Da. Dalteparin sodium is produced through nitrous acid depolymerisation of sodium heparin from porcine intestinal mucosa. It is composed of strongly acidic sulphatcd polysaccaride chains with an average molecular weight of 4000–6000 and about 90% of the material within the range 2000–9000 Da.

Other low molecular weight heparins on the market are e.g. Klexane® (enoxaparin), Fraxiparine® (nadroparin), Clivarin® (reviparin) and Innohelp® (tinzaparin). Different uses within the therapeutic area have been suggested for low molecular weight heparin such as treatment of diabetic nephopathy and diabetic neuropathy (EP513513), treatment of chronical renal insufficiency (EP710483), inhibition of TNF-α secretion (WO9219249) and treatment of inflammatory or immunological diseases (WO9418988). During the past tell years considerable progress has been made in the medical treatment of patients with acute myocardial infarction as well as unstable and stable angina pectoris. In this type of patients with coronary artery disease the risk of total occlusion and development of a larger myocardial infarction can be reduced by 50% by aspirin (1, 2, 3) and by another 65% by heparin infusion or weight-adjusted s.c. dalteparin, a low molecular weight heparin, for six days (1, 2, 4, 5), reducing the myocardial infarction rate to 1–2% during this period During the short-term dalteparin/heparin treatment, symptoms subside (2, 5) but a significant stenosis often remains in the artery because of the pre-existing atherosclerotic lesion and/or remaining thrombotic material (6–8). Still, after the acute treatment period the risk of a new myocardial infarction is around 10% after six weeks and 15% after six months, despite conventional treatment. Therefore, a long-term pharmaceutical and/or interventional policy is urgently needed in these patients to reduce the long-term event rate.

The FRISC study (5) demonstrated that treatment with a low molecular weight (l.m.w.) heparin (dalteparin, Fragmin®) influenced the risk of death/myocardial infarction. It was shown that Fragmin® 120 IU/kg/12 h for six days compared to placebo reduced myocardial infarction by 63%, recurrent angina and the need for urgent revascularisation by 50% during the initial six days. During the continued long-term treatment using 7,500 IU/24 h for forty days or corresponding placebo the absolute reduction in event rates was maintained.

However, early after the lowering of the dose at six days there were indications of reactivation of the disease.

Numerous studies have demonstrated that signs of ischemia at ambulatory monitoring or stress tests might identify patients at an increased risk of subsequent cardiac events (9–14).

Most of these studies were performed without the use of modern medication, such as aspirin, β-blockers, ACE-inhibitors and lipid lowering drugs. At the present time the utilisation and timing of revascularisation in these patients is variable and very little guidance can be obtained from the presently available scientific reports. Inadequate use of modern protective medication and invasive procedures might result in considerable consequences both for the patients and the costs of medical care. Therefore, it seemed essential to explore further the protective effects of prolonged intense antithrombotic medication. Of equal interest has been to elucidate whether a direct invasive approach with early coronary revascularisation had any advantages compared to a stepwise selective approach with invasive procedures only at recurring or incapacitating symptoms or ischemia in patients with unstable coronary artery disease, who received optimal protective medication.

ABBREVIATIONS AND DEFINITION OF TERMS

| | |
|---|---|
| ACE | angiotensin converting enzyme |
| Angiography | Study of vessels |
| Anti-ischemic drugs | defined as β-blockers, nitrates (long- and short-acting), calcium antagonists |
| ASA | aspirin, acetyl salicylic acid |
| BMI | body mass index |
| CABG | coronary artery bypass grafting |
| CAD | coronary artery disease |
| Lipid lowering drugs | defined as statins, fibrates and other lipid lowering drugs |
| l.m.w. heparin | low molecular weight heparin |
| MI | myocardial infarction |
| Other cardiovascular drugs | defined as ACE-inhibitors, digitalis, diuretics drugs |
| p.o. | per oral |

-continued

| ABBREVIATIONS AND DEFINITION OF TERMS | |
|---|---|
| PTCA | percutaneous transluminal coronary angioplasty |
| p-value | Cochran-Mantel-Haenszel test |
| Revascularisation, Rev | restoration of blood supply by surgical intervention e.g. balloons and/or by-pass |
| s.c. | subcutaneous |

Figure 2:
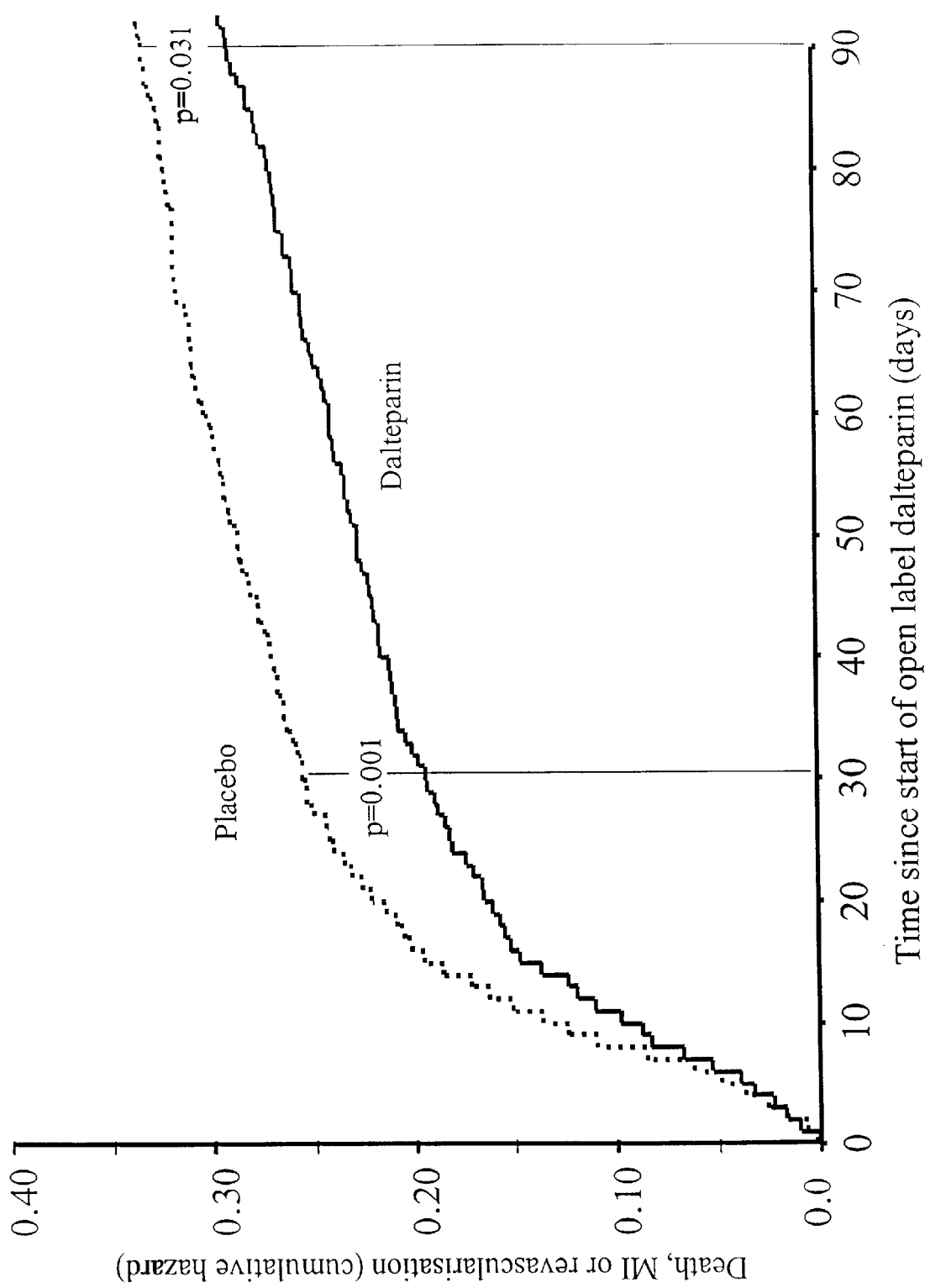
Figure 3:
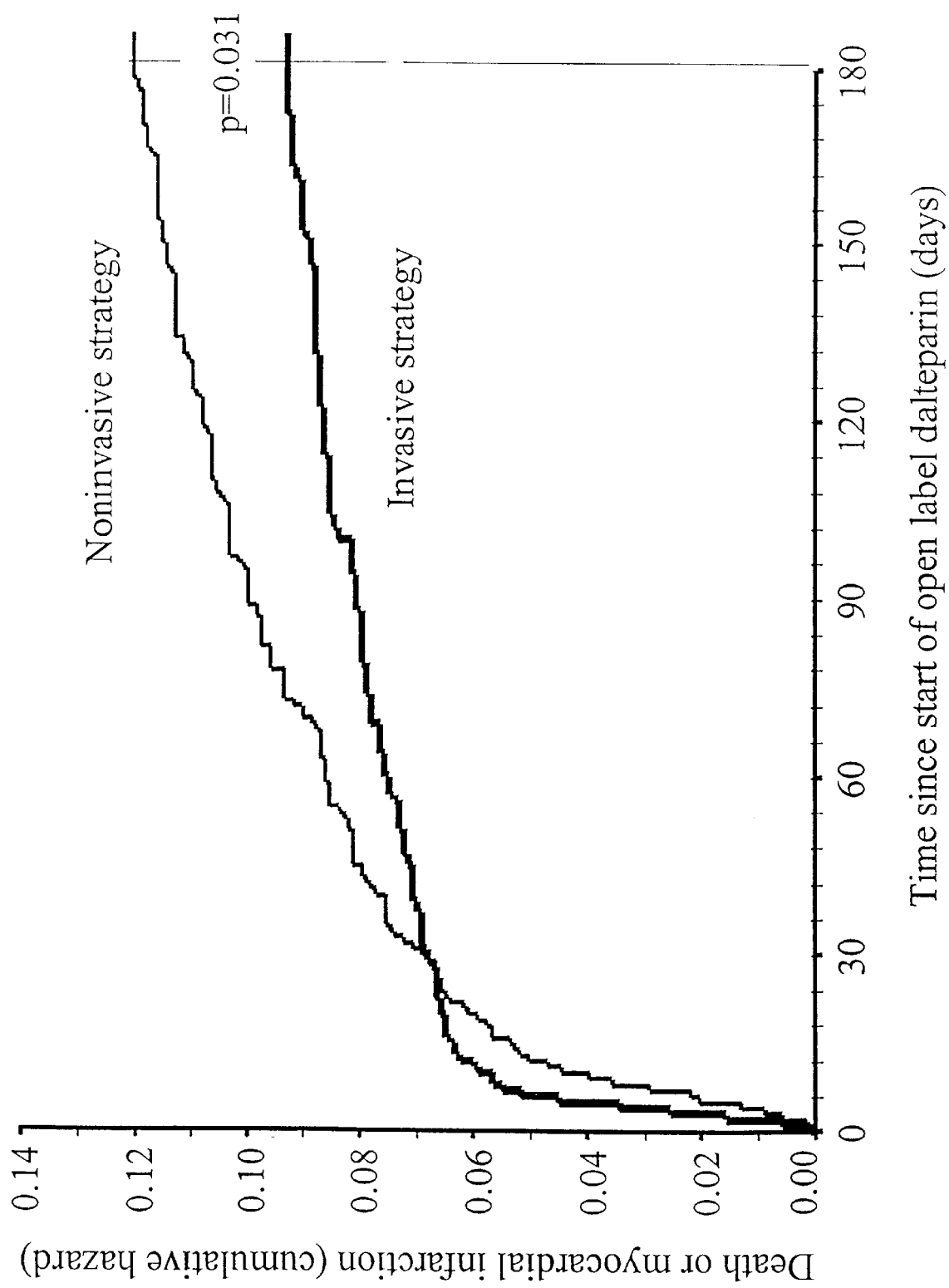

Non-invasive policy = stepwise selective approach with coronary angiography and coronary revascularisation only at recurring br incapacitating symptoms or severe ischemia at exercise test
Invasive policy = direct invasive approach with early coronary angiography and revascularisation
FIGS.
FIG. 1    Probability of death or MI during treatment up to 3 months
FIG. 2    Death, MI or revascularisation (comulative hazard)
FIG. 3    Death or MI (comulative hazard)

THE INVENTION

The invention relates to a method for treatment of unstable coronary artery disease, which is characterised by an early revascularisation together with administration of a low molecular weight heparin. Preferably the low molecular weight heparin is administered up to revascularisation.

Clinical benefit has been shown for treatment up to 60 days, but the revascularisation should be done as early as possible, and more preferably before 30 days.

The methods are also useful for treatment of unstable angina, for not worsening chest pain and for treatment of non-Q-wave myocardial infarction (mild heart attack).

The present study compared the efficacy of prolonged (three months) treatment with Fragmin with that of short term (five to seven days) treatment in patients with unstable coronary artery disease. During the first five to seven days, known as the open acute phase of this double blind randomized clinical trial, all 2,267 patients received 120 IU/kg/12h of Fragmin. Durinig the prolonged (up to 90 days) double blind phase, 2,105 patients were randomized to treatment with either subcutaneous Fragmin at a dose of 5,000 or 7,500 IU twice daily or placebo.

From Day 1 to 150, the incidence of death and/or MI was statistically significant between the two treatment strategies in favour of the early invasive policy (p=0.031).

It has been found that prolonged treatment with Pharmacia & Upjohni's low molecular weight heparin, Fragmin® (dalteparin sodium injection) for up to 30 days demonstrates a 47 percent reduction in the incidence of death or heart attack in patients who suffered unstable coronary artery disease, which includes unstable angina (worsening chest pain, often when at rest) and non-Q-wave myocardial infarction (mild heart attack).

Results from the study below shows that after 30 days of treatment with Fragmin, the incidence of death/myocardial infarction in patients was 3.1 percent compared with 5.9 percent for patients who received placebo after the acute treatment phase (p=0.002). Continuing the treatment with Fragmin to 90 days showed no further effect.

It has also been found that early protective effects of continued dalteparin treatment could be utilised to reduce the risk of events in unstable CAD patients waiting for invasive procedures. These findings of the study are important not only because of the reduction in mortality and morbidity, but also because they suggest that the combined use of a low molecular weight heparin and surgical intervention—balloon angioplasty and coronary bypass— offers patients an improved outcome. Treating patients who suffer from unstable coronary artery disease with a low molecular weight heparin may provide both doctor and patient with the flexibility to map out further treatment strategies.

Reference to the study is made to Lancet, Vol. 354, 1999, pages 701–707 and 708 –715.

EXAMPLE

Patients with Noni-Q-wave Myocardial Infarction or Unstable Angina have been Compared:

A. Prolonged treatment with Fragmin® 5,000 alternatively 7,500 IU or placebo s.c. twice daily for three months, B. Two policies of coronary interventions (referred to as 'invasive' or 'non-invasive', regarding the risk of death, non-fatal myocardial infarction, cardiac symptoms and costs.

During the study period the patients received optimal therapy using aspirin, 1.m.w. heparin (in the acute treatment period), -beta-blockade—calcium inhibitors—organic nitrates—ACE—inhibition at symptoms or signs of left ventricular dysfunction. Metabolic corrections including lipid lowering drugs and life-style changes were suggested.

Study drugs: Manufactured and supplied by Pharmacia & Upjohn AB, Sweden.

Reference product : Placebo syringes 0.3 mL and 0.2 mL, respectively, containing sodium chloride dissolved in water to a concentration of 9 g/L, for s.c. injection were provided. The placebo syringes were identical in appearance with the active Fragmin® syringes. The placebo syringes were manufactured and supplied by Pharmacia & Upjohn AB, Sweden.

Primary Objective

The primary objective of the study was to compare the long-term treatment (after open Fragmin® s.c.120 IU/kg/12 h—maximum dose 10,000 IU/12h—during the acute period) for three months using either weight-adjusted Fragmin® 5000 alternatively 7500 IU with. placebo s.c. twice daily concerning the incidence of death or acute myocardial infarction from start of double-blind treatment and until day 90.

The primary objective was to be assessed using data from the patients treated according to the non-invasive policy, either because they were randomly assigned to it or because they were contraindicated to the early invasive revascularisation policy.

Secondary Objective

The secondary objective was to compare an invasive approach with early coronary angiography and revascularisation ('invasive policy') with a stepwise selective approach with coronary angiography and revascularisation only at recurring or incapacitating symptoms or severe ischemia at exercise test ('non-invasive policy'), concerning the incidence of death or acute myocardial infarction from start of Fragmin® 120 IU/kg/12 h or heparin until the six months' visit (180 days after start of acute therapy with Fragmin® or heparin).

During the first three months the patients were blindly treated with either Fragmin® 5,000 alternatively 7,500 IU/12 h (depending on sex and weight) or placebo, after Fragmin® s.c. 120 IU/kg/12 h—maximal dose 10,000 IU/12 h—during the acute period.

Tertiary Objective

The tertiary objective was to compare the long-term treatment of Fragmin® 5000 alternatively 7500 IU with placebo s.c. twice daily, concerning the incidence of death or acute myocardial infarction from start of Fragmin® 120 IU/kg/12 h or heparin until day 90. The tertiary objective was to be assessed using data from all patients randomly included in the study.

The study comprised the following six groups:

No contraindications to revascularisation:
   Non-invasive policy+Fragmin®
   Non-invasive policy+placebo
   Invasive policy+Fragmin®
   Invasive policy+placebo
Contraindications to revascularisation:
   Non-invasive+Fragmin®
   Non-invasive+placebo Day 1 was defined as the start of open Fragmin® 120 IU/kg/12 h or heparin infusion.

Treatments Administered and Interventional Procedures

Acute Period

All patients, preferably on admission, were to be treated with Fragmin® ampoules (open Fragmin® of 10,000 IU, using a dose of 120 IU/kg/12 h up to a maximum dose of 10,000 IU/12 h). The open acute treatment was to be given to all patients for a minimum of five days. until exercise test had been performed (5–7 days) in the non-invasive policy group, and until revascularisation (within 7 days) in the invasive policy group. If exercise test or revascularisation was done before day 5, the open Fragmin® treatment was continued so that the minimum duration of treatment was five days. If urgent angiography/revascularisation was required in the non-invasive group, open Fragmin® 120 IU/kg/12 h was to be given until revascularisation.

The injections were preferably to be given at 8 a.m. and 8 p.m.±2 hours, but the time between the first and second injection could vary depending on the time of admission. During the acute period aspirin, beta-blockade and, if required, nitroglycerin infusion and other drugs for optimal therapy should be given.

Measurements of Treatment Compliance

During the open treatment period, the number of injections given were recorded. Patients treated according to a non-invasive policy, who needed urgent revascularisation, remained on open Fragmin® until the invasive procedure was done. The number of days with open Fragmin®/heparin treatment was approximately the same in the three treatment policy groups with a median of six days.

After the open treatment period the patients started double-blind randomised s.c. injections with Fragmin®/placebo.

The treatment was temporarily stopped in connection with PTCA or CABG.

Prolonged Fragmin®/placebo treatment period

After the acute period with open s.c. Fragmin® 120 IU/kg/12 h treatment, the patients started double-blind randomised s.c. injections comparing weight adjusted Fragmin® every 12 hours with corresponding placebo injections every 12 hours. The weight adjusted Fragmin®) dose was

| Women weighing | <80 kg | 5,000 IU |
|---|---|---|
| | ≧80 kg | 7,500 IU |
| Men weighing | <70 kg | 5,000 IU |
| | ≧70 kg | 7,500 IU |

Single dose syringes were used. The treatment was continued so that the total (acute+prolonged) treatment period was 3 months (90–97 days).

Direct Invasive Approach with Early Coronary Angiography/Revascularisation (invasive policy or when early revascularisation was required in non-invasive policy) Coronary angiography was to be performed as soon as possible, and revascularisation by PTCA or CABG within seven days from start of open Fragmin® s.c. or i.v. heparin infusion.

An Early Invasive Versus a Non-invasive Policy

The intention of the invasive policy was to perform coronary angiography and revascularisation, if needed, as quickly as possible and within seven days. Revascularisation using PTCA or CABG was to be attempted, if there was at least one major coronary artery with a ≧70% stenosis. The non-invasive policy recommended coronary angiography and revascularisation at recurrent symptoms, severe ischemia or reinfarction.

Number of days to performed invasive procedures was calculated from first Fragmin/heparin injection until first angio/PTCA/CABG.

RESULT

Efficacy Results and Tabulations of Individual Patient Data

1–6 months result of open+double-blind phase

| Variable | Dalteparin | Placebo | p |
|---|---|---|---|
| Death-MI | 1129 | 1121 | |
| 1 month | 6.2% | 8.4 | 0.048 |
| 3 months | 10.0% | 11.2% | 0.34 |
| 6 months | 13.3% | 13.1% | 0.93 |

The result of probability of death or MI during double blind treatment period up to three months is illustrated in FIG. 1.

| Variable | Dalteparin | Placebo | p |
|---|---|---|---|
| Death + MI + Rev. | 1129 | 1121 | |
| 1 month | 19.4% | 25.7% | 0.001 |
| 3 months | 29.1% | 33.3% | 0.031 |
| 6 months | 38.6% | 39.9% | 0.50 |

Death, MI or revascularisation (comulative hazard) up to three months is illustrated in FIG. 2.

In the total randomised cohort, including both the open label and double-blind treatment periods, there was a significant 4.3% absolute and 13% relative reduction in the triple composite of death, myocardial infarction or revascularisation. During the first month there were significant reductions of both the double 6.2% versus 8.4% and triple endpoints 19.4% versus 25.7% in the dalteparin group. fhere remained no significant differences at 6 months.

Death and/or myocardial infarction (MI) after 6 months in the invasive and the noninvasive groups. Revascularisation was performed before seven days treatment with Fragmin®

|  | Invasive N = 1207 | Noninvasive N = 1226 | p |
|---|---|---|---|
| Death and/or MI | 9.4% | 12.1 | 0.031 |
| MI | 7.8% | 10.1% | 0.045 |
| Death | 1.9% | 2.9% | 0.10 |

Death or MI (comulative hazard) up to three months is illustrated in FIG. 3.

There was a significant 22% relative 2.7% absolute reduction in death and myocardial infarction in the invasive compared to the noninvasive group after 6 months.

Long-term dalteparin administration lowers the risk of death. MI and revacularisation in unstable CAD at least during the first month of therapy. These early protective effects could thus be used to lower the risk of events in patients waiting for invasive procedures. An early invasive approach should be the preferred strategy in most patients with unstable CAD.

References

1. Theroux P, Quimet H, McCans J, et al: N Engl J Med 1988;319:1105–1111
2. Theroux P, Waters D, Qi S, et al: 1993;88:2045–2048
3. The RISC Group. Lancet 1990;336:827–830
4. Cohen M, Adams P C, Parry G, et al. Circulation 1994;89:81–88
5. FRISC Study Group (FRISC). Lancet, 1996;347:561–568
6. Feldman R I.Am J Cardiol 1987;59:187–1190
7. Ambrose J A, Hjemdahl-Monsen C E, Corrico S, et al. Am J Cardiol 1988:61:244–247
8. Williams A E, Freeman M R, Chisholm R J, et al. Am J Cardiol 1988;62:1024–1027
9. Gottlieb S O, Weisfeldt M L, Onyang, P, et al. N Engl J Med 1986,314:1214–1219
10. Larsson H, Jonasson I, Ringqvist I, et al. Eur Heart J 1992;112:207–212
11. Gibson R S, Beller G A, Gheroghiade M, et al. Circulation 1986;73:11 86–1198
12. Butman S M, Olson H G, Gardin J. et al. J Am Coll Cardiol 1984;4:667–673
13. Sia S T B, Macdonald P S, Horowitz J D, et al. Amn J Cardiol 1986;57:738–744
14. Nyman I, Larsson H, Areskog M, et al and the RISC Study Group: Am Heart J 1992;123:324–331

What is claimed is:

1. A method for treating unstable coronary artery disease, comprising:
   a) administering a low molecular weight heparin;
   b) conducting a coronary angiography; and
   c) after step (b), performing a revascularisation procedure, wherein the low molecular weight heparin is administered up to the revascularisation procedure.

2. The method of claim 1 wherein the revascularisation procedure is performed up to 7 days from the beginning of the administration of the low molecular weight heparin.

3. The method of claim 2 wherein the low molecular weight heparin is administered at a level of 120 IU/kg every 12 hours.

4. The method of claim 1 wherein the low molecular weight heparin is administered for up to 60 days.

5. The method of claim 1 wherein the low molecular weight heparin is administered for up to 30 days.

6. A method for treating unstable angina, comprising:
   a) administering a low molecular weight heparin;
   b) conducting a coronary angiography; and
   c) after step (b), performing a revascularisation procedure, wherein the low molecular weight heparin is administered up to the revascularisation procedure.

7. The method of claim 6 wherein the revascularisation procedure is performed up to 7 days from the beginning of the administration of the low molecular weight heparin.

8. The method of claim 7 wherein the low molecular weight heparin is administered at a level of 120 IU/kg every 12 hours.

9. The method of claim 6 wherein the low molecular weight heparin is administered for up to 60 days.

10. The method of claim 6 wherein the low molecular weight heparin is administered for up to 30 days.

11. A method for treating non-Q-wave myocardial infarction, comprising:
    a) administering a low molecular weight heparin;
    b) conducting a coronary angiography; and
    c) after step (b), performing a revascularisation procedure, wherein the low molecular weight heparin is administered up to the revascularisation procedure.

12. The method of claim 11 wherein the revascularisation procedure is performed up to 7 days from the beginning of the administration of the low molecular weight heparin.

13. The method of claim 12 wherein the low molecular weight heparin is administered at a level of 120 IU/kg every 12 hours.

14. The method of claim 11 wherein the low molecular weight heparin is administered for up to 60 days.

15. The method of claim 11 wherein the low molecular weight heparin is administered for up to 30 days.

* * * * *